United States Patent [19]

Lindholm

[11] Patent Number: 5,217,008
[45] Date of Patent: Jun. 8, 1993

[54] CRICOTHYROIDOSTOMY TUBE

[75] Inventor: Carl-Erik Lindholm, Uppsala, Sweden

[73] Assignee: Willy Rusch AG, Waiblingen, Fed. Rep. of Germany

[21] Appl. No.: 800,926

[22] Filed: Dec. 4, 1991

[30] Foreign Application Priority Data

Dec. 10, 1990 [SE] Sweden .................. 9003933

[51] Int. Cl.⁵ .......................................... A61M 16/00
[52] U.S. Cl. .......................... 128/207.14; 128/200.26
[58] Field of Search .................. 128/207.14, 207.15, 128/207.16, 207.17, 207.29, 911, 912, 200.26; 600/264, 96

[56] References Cited

U.S. PATENT DOCUMENTS

| | | |
|---|---|---|
| 3,476,113 | 11/1969 | Tarsitano . |
| 3,906,956 | 9/1975 | Gilbert .................. 128/207.29 |
| 4,677,978 | 7/1987 | Melker .................. 128/207.29 |

FOREIGN PATENT DOCUMENTS

1040425  8/1966  United Kingdom .

Primary Examiner—William H. Grieb
Assistant Examiner—Raleigh Chiu
Attorney, Agent, or Firm—Keck, Mahin & Cate

[57] ABSTRACT

A coniostomy tube intended for insertion through the front wall of the larynx between the bottom edge of the thyroid cartilage and the upper edge of the front part of the cricoid cartilage includes a pre-shaped curved tubular pipe having a substantially straight patient-end section, a pipe connector and an intermediate tube section which is curved through substantially 100°. At least that part of the tube which extends through the opening between the thyroid cartilage and the cricoid cartilage has a substantially oval cross-sectional shape with the small axis of the ovality positioned in the curvature plane of the tube. This ovality is in the range of 1:1.2 to 1:1.35. The curved intermediate section of the tube preferably has essentially the same ovality and ovality orientation, and the tube may also have the same oval cross-sectional shape along the whole of its length. The outer pipe connector of the tube preferably forms an angle of 80° with the substantially straight patient-end section of the tube.

11 Claims, 1 Drawing Sheet

CRICOTHYROIDOSTOMY TUBE

The present invention relates to a coniostomy tube which is intended for insertion through an opening extending through the front wall of the larynx, between the front part of the cricoid cartilage and the thyroid cartilage. The tube includes a pre-shaped tubular section which is bent generally to an L-shape in one plane, and the tubular section includes a generally straight section which terminates at the patient-end of the tube, a curved intermediate section, and a substantially straight end section which terminates at the machine end of the tube and extends out through said opening.

This tube is sometimes referred to in the U.S.A. as a "cricothyroidostomy tube", while the term "coniostomy tube" is used in other English-speaking regions. Tubes of this special kind are not manufactured especially for this purpose, but instead existing tracheostomy tubes are used as an "emergency solution".

It is often preferred to form an opening in membrana cricothyreoidea and to introduce a tube through the opening between the cricoid cartilage and the thyroid cartilage. This is because membrana cricothyreoidea lie closer to the skin and because it is easier to form surgically respiratory passageways to the respiratory tract or airway in this way than through the trachea or windpipe. Another advantage is that the opening to the airway is located further away from the surgical incision used to open the thorax in the median line in certain surgical operations performed in the thoracic cavity.

Tracheostomy tubes have recommended standards; see ISO 5366/2-1985.

A conventional tube may consist of a plastic tube which is bent to substantially a right angle in the central region thereof, while maintaining a substantially circular cross-section, the tube preferably being provided at the patient-end with an inflatable collar which provides a seal between the trachea and the tube, and the machine end of the tube is fitted with a neck or throat plate and a pipe connector.

Despite the advantage of providing surgically an easier passage to the airway or respiratory tract, the use of tracheostomy is not problem-free.

For example, the available opening between the cartilage walls of the larynx is limited and defined by the upper edge of the front part of the cricoid cartilage and the bottom edge of the front part of the thyroid cartilage. In order to prevent excessively powerful resistance to the flow of air through the tube, it has been necessary to choose an outer tube-diameter in the order of 9.5-10 mm in the case of males and in the order of 8-8.5 mm in the case of females.

It has also been observed that clamping or pinching injuries are often sustained in the larynx, in the vicinity of the larynx opening through which the tube is inserted, and that patients frequently suffer a change of voice subsequent to removal of the tracheostomy tube.

An object of the present invention is primarily to provide a tube of the aforesaid kind with which the risk of afflicting clamping injuries to the patient's larynx and the risk of voice changes of the patient subsequent to removal of the tube are reduced, while minimizing the resistance to air flow in the tube.

Other advantages afforded by the invention will be apparent from the following description.

The object of the invention is achieved with a coniostomy tube for insertion into the larynx of a patient through an opening formed through the front wall of the larynx between the front part of the cricoid cartilage and the thyroid cartilage, said tube including a pre-shaped tubular piece which has a substantially straight section which connects with a patient-end of the tube, an intermediate, curved section and a substantially straight section which connects with a machine-end of the tube, said two substantially straight tube-sections lying substantially in a common plane, wherein at least that part of the tube which is intended to extend through said opening has a substantially oval shaped cross-section when seen perpendicularly to the tube axis, wherein the small axis of the oval cross-section is positioned substantially in the curvature plane of the tube, and wherein the external ovality of the oval cross-section is in the region of 1:1.2 to 1:1.35.

In the case of a tube of the aforedescribed kind, the aforesaid object is achieved with a tube of which at least that part which is intended to pass through the opening between the cartilage parts has a substantially oval cross-sectional shape with the small axis of the oval orientated in the aforesaid curvature plane of the tube, wherein the oval cross-section of the tube perpendicular to the tube axis has an ovality in the region of 1:1.2 to 1:1.35.

This ovality preferably lies in the range of 1:1.24 to 1:1.30. In the case of males, this ovality is preferably about 1:1.24, while in the case of females, the ovality will preferably be about 1:1.27.

The cross-sectional area of the tube at that part of the tube which passes through the opening in the larynx is preferably chosen to provide an optimally large through-flow of air, while minimizing the risk of the tube clamping against the cartilage parts that define the opening through the larynx.

Because of the inventive ovality of the tube, the tube insertion section has a cross-sectional shape which, on the one hand, enables the free space between the lower edge of the thyroid cartilage and the upper edge of the front part of the cricoid cartilage to be used to a maximum and, on the other hand, minimizes the risk of local clamping injury to those parts of the cartilage which lie around the periphery of the opening and also minimizes the risk of deformation to the larynx such as to cause changes in the nature of the patient's voice. It has been found particularly essential to avoid changes in the distance between the upper and the lower edge of the penetration opening through the larynx wall, since a decrease in this distance can result in raising the tone of the voice (giving the voice a feminine tone) which would be unacceptable in the case of male patients, while an increase in said distance has the opposite effect.

Ovality is defined as the ratio of the outer large-axis dimension of the tube cross-section to the outer small-axis dimension, taken at right angles to the tube axis. In addition to the insertion region of the tube, the curved intermediate section of the tube may also have an ovality of the aforedescribed configuration, so as to enable an angular change between the two generally straight end-parts of the tube to be more easily effected, such as when adapting the tube to the anatomy of the patient.

For example, in the case of adult males, it has been found suitable to use tubes whose insertion sections have an external ovality in which the external measurements of the small/large axis are 8.5-10.5 or 9-11 mm. Corresponding external tube measurements for females are 7.5-9.5 or 8-10 mm. The tube will normally have a wall thickness in the region of 1-1.5 mm and will include a helical insert made of metal wire or some other material, for instance nylon, embedded in the tube wall so as to hold the lumen of the tube open, even in the curved region of the tube when the tube is given a more pronounced bend.

According to one preferred embodiment of the invention, the outer tube-end (the machine-end) is fitted with a pipe connector whose axial direction preferably forms a slightly acute angle with the substantially straight patient-end section of the tube. This angle is preferably about 70°-80°.

The pipe connector is preferably positioned at an angle of about 20°-30° to the generally straight tube section that passes through the front wall of the larynx. This avoids interference with the patient's chin while the tube itself will still bend at an obtuse angle, therewith facilitating insertion of the tube and also the insertion of suction catheters through the tube. The connector pipe preferably has a small length of about 16 mm and is suitably constructed in other respects in accordance with ISO 5356-1 for connection to a respirator either directly or via a unit in which respiration air is moistened, heated and filtered.

The invention will now be described in more detail with reference to an exemplified embodiment of the inventive coniostomy tube illustrated in the accompanying drawing, in which FIG. 1 is a schematic sectional view taken through the symmetry plane of the neck region of a patient and illustrates an inventive tube inserted into the patient's trachea;

Figure 1:
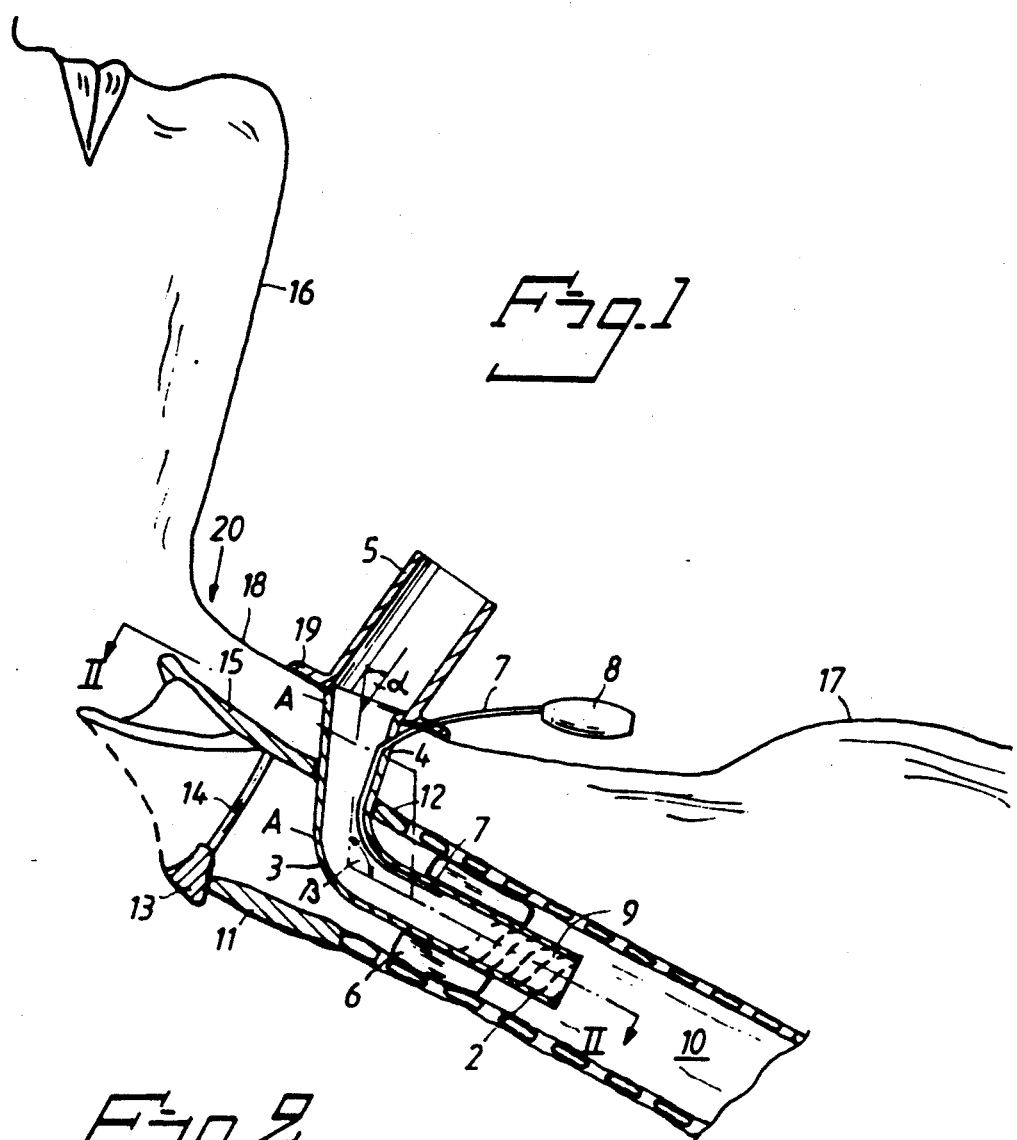

FIG. 1 is a schematic, sectional view taken in the symmetry plane through the neck region of a patient, the patient's chin, throat and chest being indicated by reference numerals 16, 18 and 17 respectively. Also shown in FIG. 1 is the patient's trachea 10 and larynx 20, including the thyroid cartilage 15, the thicker rearward part 11 of the cricoid cartilage and the thinner, low forward part 12 thereof. FIG. 1 also illustrates the arytenoid bone 13 and a vocal cord 14. Located on the front side between the thyroid cartilage 15 and a forward cricoid-cartilage part 12 is a membrane, membrana cricotyreoidea, which lies close to the skin of the throat or neck and which can be easily opened surgically to enable a coniostomy tube (or tracheostomy tube) to be inserted through this opening and into the trachea 10.

The coniostomy tube includes a first, generally straight section 2, which connects to the patient-end of the tube, an intermediate, curved section 3 and a generally straight section 4 which connects with the machine-end of the tube and which is defined by a connector pipe 5.

The connector pipe 5 is fitted with a neck plate 19 which is intended to be brought into abutment with the patient's neck and fixed in position by means of a band or strap which passes around the neck of the patient.

The tube 2, 3, 4 is made of a plastic material or of some other material suitable for this purpose, and has embedded or embodied therein a helical metallic wire or a filament made of some other material 9, which prevents the tube from collapsing should, for some reason or other, the angle $\beta$ between the sections 2, 4 of the tube become too small when inserting and positioning the tube.

An inflatable sealing collar 6 surrounds the insertion end 2 of the tube and can be inflated by passing fluid through a passageway which extends through the tube wall and is connected to a pilot bladder 8 provided with a check valve, by means of a connecting line 7.

When the angle $\alpha$ defined by the axis of the pipe connector 5 and the axis of the tube section 4 is in the order of 20°-30°, the risk of the patient's chin 16 interfering with the pipe connector 5 and the equipment associated therewith is minimized, even though the patient should be corpulent, with the chin 16 of the patient located closer to the connector pipe 5 than is shown in FIG. 1.

The angle $\beta$ may be in the order of 100° and it is preferred that the angle between the pipe connector 5 and the tube section 2 is about 70°-80°.

Figure 2:
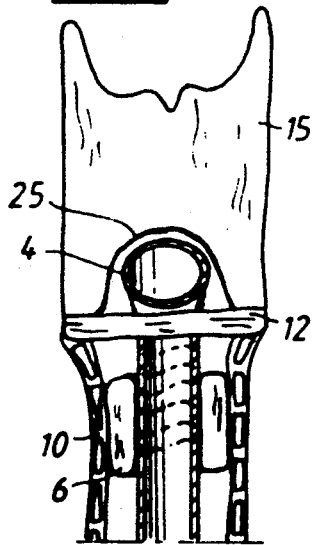
FIG. 2 is a schematic sectional view taken on the line II—II in FIG. 1.

As will be seen from FIG. 2, the bottom edge 25 of the thyroid cartilage 15 has a shape which is similar to the illustrated oval cross-sectional shape of the tube section 4.

It will be seen from FIG. 1 that the tube section 4 has the aforesaid oval cross-sectional shape along that longitudinal part of the tube section which passes through the front wall of the larynx, for example in that section which lies between the marks A in FIG. 1. It will be seen from FIG. 2 that the tube section 4 substantially adjoins the upper edge of the forward cricoid-cartilage part 12, the tube 4 thus having an area which is optimal with respect to the air throughflow.

Figure 3:
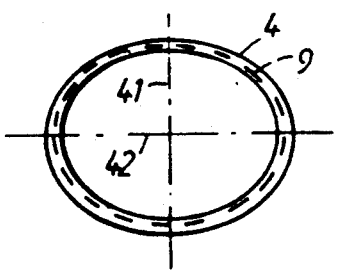
FIG. 3 is a schematic view of the cross-sectional shape of the inventive tube in that section of the tube which passes through the front wall of the larynx in the opening between the thyroid cartilage and the cricoid cartilage.

It will be seen from FIG. 3 that at least that part of the tube section 4 which passes the opening between the thyroid cartilage 15 and the cricoid cartilage 12 has an elliptically oval form, the small axis 41 of which oval coincides with the bending plane of the tube and which is intended to lie in the symmetry plane of the patient. The Figure also shows the large axis 42 of the oval shape. A helical metallic wire or a helical filament of some other appropriate material is embedded in the wall of the tube section 4.

The outer ovality of the insertion region of the tube lies in the range 1:1.2–1:1.35, preferably 1:1.24–1:1.30. In the case of male patients, this ovality is suitably about 1:1.24, and for female patients, preferably about 1:1.27.

In the case of male patients, the outer measurements of the insertion region of the tube are preferably 10.5 and 8.5 mm respectively (or 11 mm and 9 mm respectively when the wall thickness if 1.5 mm) along the large axis and the small axis respectively, whereas in the case of female patients, the outer measurements are preferably 9.5 and 7.5 mm respectively (or 10 mm and 8 mm respectively when the wall thickness is 1.5 mm). The wall thickness of the tube is preferably about 1-1.5 mm. The wall thickness of the illustrated exemplifying embodiment is about 1.25 mm.

The tube preferably has an ovality of substantially the same orientation as in the insertion section, along the curved central region of the tube, so as to afford reduced resistance to bending between the two generally straight end sections of the tube. The ovality of the tube may also be maintained along the full length of the tube.

I claim:

1. A cricothyroidostomy tube for insertion into the larynx of a patient through an opening formed through the front wall of the larynx between the front part of the cricoid cartilage and the thyroid cartilage, said tube including a pre-shaped tubular piece which has a first substantially straight section which connects with a patient-end of the tube, an intermediate, curved section and a second substantially straight section which connects with a machine-end of the tube, said two substantially straight tube-sections lying substantially in a common plane, wherein at least that part of the tube which is intended to extend through said opening has a substantially oval shaped external cross-section when seen perpendicularly to the tube axis, wherein the small axis of the oval cross-section is positioned substantially in the curvature plane of the tube, and wherein the external ovality of the oval cross-section is in the region of 1:1.2 to 1:1.35.

2. A tube according to claim 1, wherein the outer cross-section area of the tube in that part of the tube which is intended to extend through said opening substantially fills the area of said opening.

3. A tube according to claim 1, wherein the external ovality is in the range of 1:1.24 to 1:1.30.

4. A tube according to claim 3, wherein a preferred external ovality is about 1:1.24.

5. A tube according to claim 3, wherein a preferred external ovality is about 1:1.27.

6. A tube according to claim 1, wherein the intermediate curved section of the tube has an oval cross-sectional shape, and wherein the small axis of the oval cross-sectional shape is positioned in the curvature plane of the tube.

7. A tube according to claim 1, wherein the tube also has an oval cross-sectional shape within remaining parts of its length.

8. A tube according to claim 1, wherein the machine-end of the tube has permanently attached thereto a connector pipe which forms with the concave curvature of the tube an angle of 20°-30° to the substantially straight machine-end of the tube.

9. A tube according to claim 1, wherein said tube is adapted for bending in the plane of curvature.

10. A tube according to claim 1, wherein said patient-end of the tube comprises an inflatable sealing collar.

11. A tube according to claim 1, wherein the entire tube has a substantially oval cross-sectional shape.

* * * * *